US009827318B2

(12) United States Patent
Sahouani

(10) Patent No.: US 9,827,318 B2
(45) Date of Patent: Nov. 28, 2017

(54) POLYMERIC PARTICLES FOR STORAGE AND DELIVERY OF ACTIVE AGENTS

(71) Applicant: 3M INNOVATIVE PROPERTIES COMPANY, St. Paul, MN (US)

(72) Inventor: Hassan Sahouani, Hastings, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 806 days.

(21) Appl. No.: 14/356,733

(22) PCT Filed: Nov. 1, 2012

(86) PCT No.: PCT/US2012/063004
§ 371 (c)(1),
(2) Date: May 7, 2014

(87) PCT Pub. No.: WO2013/077981
PCT Pub. Date: May 30, 2013

(65) Prior Publication Data
US 2014/0309314 A1    Oct. 16, 2014

Related U.S. Application Data

(60) Provisional application No. 61/561,997, filed on Nov. 21, 2011.

(51) Int. Cl.
| | | |
|---|---|---|
| *C08J 9/26* | (2006.01) | |
| *C08F 2/16* | (2006.01) | |
| *C08F 222/10* | (2006.01) | |
| *A61K 47/32* | (2006.01) | |
| *C08F 220/30* | (2006.01) | |
| *A01N 25/10* | (2006.01) | |
| *A61K 31/166* | (2006.01) | |

(52) U.S. Cl.
CPC .............. *A61K 47/32* (2013.01); *A01N 25/10* (2013.01); *A61K 31/166* (2013.01); *C08F 2/16* (2013.01); *C08F 220/30* (2013.01); *C08F 222/1006* (2013.01); *C08J 9/26* (2013.01); *C08J 2201/0462* (2013.01); *C08J 2333/04* (2013.01)

(58) Field of Classification Search
CPC .......... C08J 9/26; C08F 2/16; C08F 222/1006
See application file for complete search history.

(56) References Cited

U.S. PATENT DOCUMENTS

| | | |
|---|---|---|
| 4,303,736 A | 12/1981 | Torobin |
| 4,743,545 A | 5/1988 | Torobin |
| 5,045,569 A | 9/1991 | Delgado |
| 5,834,577 A * | 11/1998 | Sojka ................. B01J 20/26 428/407 |
| 5,908,896 A | 6/1999 | Mayer |
| 6,720,007 B2 | 4/2004 | Walt |
| 7,674,836 B2 | 3/2010 | Rasmussen |
| 7,683,100 B2 | 3/2010 | Rasmussen |
| 8,338,496 B2 | 12/2012 | Rasmussen |
| 8,349,906 B2 | 1/2013 | Rasmussen |
| 2005/0143477 A1* | 6/2005 | Soderman ........... B01D 15/325 521/50 |
| 2010/0104647 A1* | 4/2010 | Ting .................... A61K 9/5026 424/489 |
| 2011/0123456 A1 | 5/2011 | Pandit |

FOREIGN PATENT DOCUMENTS

| | | |
|---|---|---|
| CN | 101293192 | 10/2008 |
| EP | 0990667 | 4/2000 |
| JP | S 60-008306 | 1/1985 |
| JP | H 05-105729 | 4/1993 |
| JP | 2002-265529 | 9/2002 |
| WO | WO 2006/133519 | 12/2006 |
| WO | WO 2007/146722 | 12/2007 |
| WO | WO 2009/061759 | 5/2009 |

OTHER PUBLICATIONS

Macintyre (Macromolecules 2004, 37, p. 7628-7636).*
Jayachandran (J. Macromol. Sci.—Polymer Reviews, C41(1&2), p. 79-94 (2001)).*
Ma, Guanghui, Series of New Polymer Materials, Polymer Microspheres Material, Editor on duty: Ding Shanglin, Material Science and Engineering Publisher Center, Chemical Industry Publisher, Jun. 2005, Beijing, China (4 pages with translation).
Yuan, "Preparation of macroporous poly(styrene-divinylbenzene) resin with linear oligomer as porogen", Chemical Engineering, Apr. 2010, vol. 38, No. 4, pp. 73-76.
Drtina, "Highly Cross-Linked Azlactone Functional Supports of Tailorable Polarity", Macromolecules, Jun. 17, 1996, vol. 29, No. 13, pp. 4486-4489.
Gokmen, "Porous polymer particles—A comprehensive guide to synthesis, characterization, functionalization and applications", Progress in Polymer Science, Jul. 23, 2012, vol. 37, pp. 365-405.
International Search Report for PCT International Application PCT/US2012/063004, dated Dec. 21, 2012, 3 pages.

* cited by examiner

*Primary Examiner* — Robert Havlin
(74) *Attorney, Agent, or Firm* — Jean A. Lown

(57) ABSTRACT

Polymeric particles are provided that have pores (i.e., free volume or voids). The polymeric particles can be used to store or deliver active agents that are adsorbed in the pores of the polymeric particles. In many embodiments, the active agents are hydrophobic. Reaction mixtures and methods of forming the polymeric particles from the reaction mixtures are also provided.

14 Claims, 2 Drawing Sheets

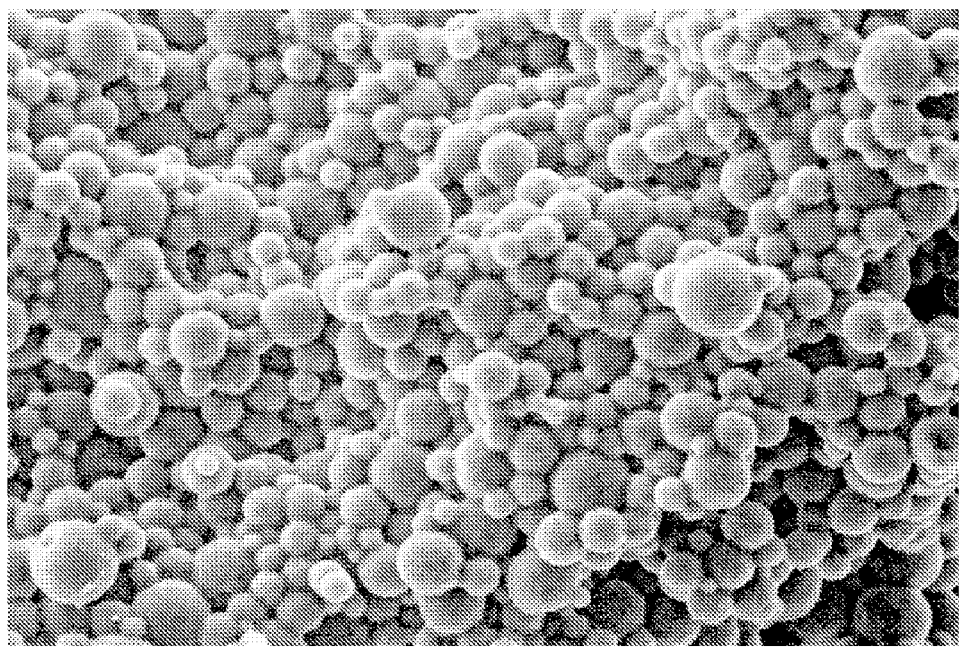
FIG. 1  50μm
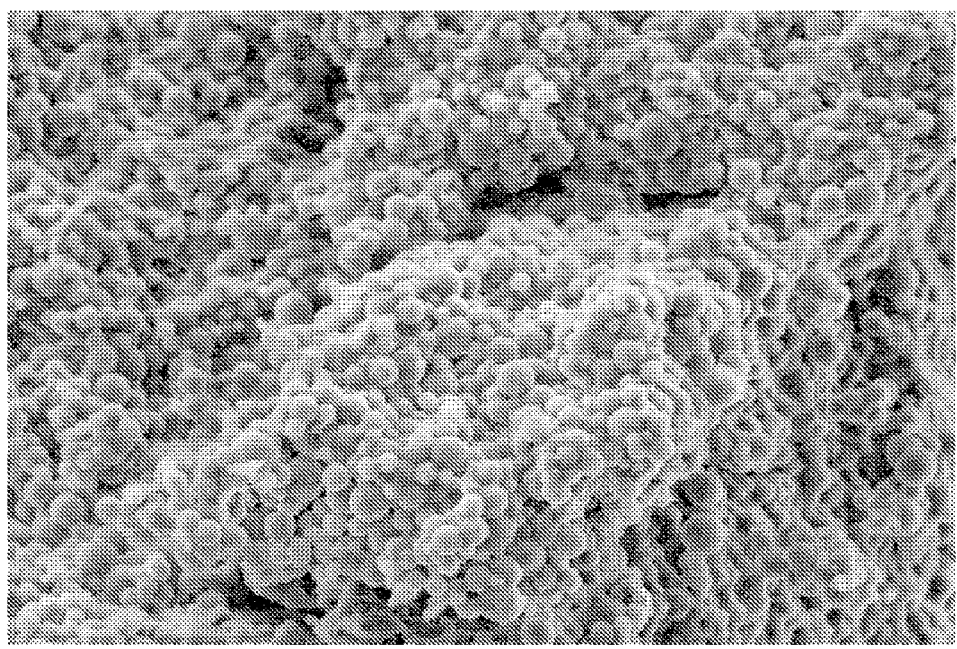
FIG. 2  50μm

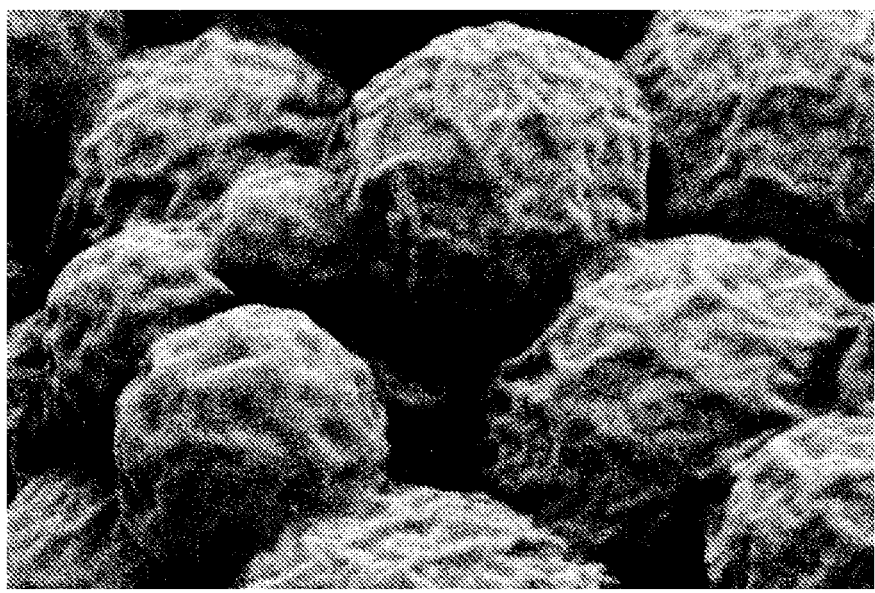
*FIG. 3*   6.00μm

POLYMERIC PARTICLES FOR STORAGE AND DELIVERY OF ACTIVE AGENTS

CROSS REFERENCE TO RELATED APPLICATIONS

This application is a national stage filing under 35 U.S.C. 371 of PCT/US2012/063004, filed Nov. 1, 2012, which claims priority to U.S. Provisional Application No. 61/561, 997, filed Nov. 21, 2011, the disclosure of which is incorporated by reference in its/their entirety herein.

FIELD

Polymeric particles are provided that have voids that can be used for the storage and delivery of various active agents.

BACKGROUND

Methods for delivering active agents are of great interest. Various particles have been developed for adsorption and delivery of different active agents. Some particles are inorganic as described, for example, in Patent Application Publication WO 2006/133519 A1 (Finnie et al.). Other particles have a polymeric shell surrounding a hollow core that can be filed with active agents. Such particles are described, for example, in U.S. Patent Application Publication 2010/0104647 A1 (Ting) and U.S. Patent Application Publication 2011/0123456 (Pandidt et al.).

SUMMARY

Polymeric particles are provided that have voids that can be used for the storage and delivery of various active agents. Reaction mixtures used to form the polymeric particles, methods of making the polymeric particles, and uses of the polymeric particles are described. The polymeric particles are often in the form of beads.

In a first aspect, a reaction mixture is provided that includes 1) a continuous phase and 2) a dispersed phase in the continuous phase. The continuous phase contains water and a polysaccharide dissolved in the water. The dispersed phase includes a) a monomer mixture and b) poly(propylene glycol). The monomer mixture contains i) a first monomer that is hydrophobic and that has an ethylenically unsaturated group and ii) a second monomer that is a poly(alkylene oxide) di(meth)acrylate and that is miscible with the first monomer. The poly(propylene glycol) has a weight average molecular weight of at least 500 grams/mole and is miscible with the first monomer and the second monomer.

In a second aspect, a method of making a polymeric particle is provided. The method includes preparing a blended composition that contains a) a monomer mixture and b) a poly(propylene glycol). The monomer mixture contains i) a first monomer that is hydrophobic and that has an ethylenically unsaturated group and ii) a second monomer that is a poly(alkylene oxide) di(meth)acrylate and that is miscible with the first monomer. The poly(propylene glycol) has a weight average molecular weight of at least 500 grams/mole and is miscible with the first monomer and the second monomer. The method further includes forming a reaction mixture by dispersing the blended composition in a continuous phase containing water and a polysaccharide dissolved in the water. The method still further includes curing the monomer mixture within the reaction mixture to form polymeric particles containing poly(propylene glycol) and then removing the poly(propylene glycol) from the polymeric particles to form pores within the polymeric particles.

In a third aspect, a polymeric particle is provided that includes a reaction product of a monomer mixture that contains i) a first monomer that is hydrophobic and that has an ethylenically unsaturated group and ii) a second monomer that is a poly(alkylene oxide) di(meth)acrylate and that is miscible with the first monomer. The polymeric particles have pores containing poly(propylene glycol) or a hydrophobic active agent.

BRIEF DESCRIPTION OF THE DRAWINGS

The invention may be more completely understood in consideration of the following detailed description of various embodiments in connection with the accompanying drawings, in which:

FIG. 1 is a scanning electron micrograph at 500× magnification of example polymeric particles prior to removal of entrapped poly(propylene glycol).

FIG. 2 is a scanning electron micrograph at 500× magnification of example polymeric particles after removal of entrapped poly(propylene glycol).

FIG. 3 is a scanning electron micrograph at 5000× magnification of example polymeric particles after removal of entrapped poly(propylene glycol).

DETAILED DESCRIPTION

Polymeric particles are provided that have pores (i.e., free volume or voids). The polymeric particles can be used to store and/or deliver active agents that are adsorbed in the pores of the polymeric particles. The polymeric particles tend to be hydrophobic and are particularly well suited for use with hydrophobic active agents. Reaction mixtures and methods of forming the polymeric particles from the reaction mixtures are also provided.

In a first aspect, a reaction mixture is provided. The reaction mixture can be used to provide polymeric particles. The reaction mixture includes 1) a continuous phase and 2) a dispersed phase in the continuous phase. The continuous phase contains water and a polysaccharide dissolved in the water. The dispersed phase includes a) a monomer mixture and b) a poly(propylene glycol). The monomer mixture contains i) a first monomer that is hydrophobic and that has an ethylenically unsaturated group and ii) a second monomer that is a poly(alkylene oxide) di(meth)acrylate and that is miscible with the first monomer. The poly(propylene glycol) has a weight average molecular weight of at least 500 grams/mole and is miscible with the first monomer and the second monomer.

The continuous phase is an aqueous medium and contains water and a polysaccharide dissolved in the water. The continuous phase is typically formulated to provide a suitable viscosity for polymerization of polymeric particles within the dispersed phase. If the viscosity of the continuous phase is too low, polymeric particles with a suitable shape (e.g., beads) will not form. If the viscosity of the continuous phase is too great, however, it can be difficult to provide the requisite shear to form a dispersed phase within the continuous phase.

Suitable polysaccharides are those that are soluble in water. The amount of the polysaccharide is often based on the solubility of the polysaccharide and the viscosity of the continuous phase containing the polysaccharide. The amount of polysaccharide is typically selected so that it is entirely dissolved in the continuous phase. In many embodiments, the continuous phase contains only water and the dissolved polysaccharide.

The continuous phase can contain up to 50 weight percent polysaccharide based on a total weight of the continuous phase. For example, the continuous phase can contain up to 40 weight percent, up to 30 weight percent, up to 25 weight percent, up to 20 weight percent, up to 15 weight percent, or up to 10 weight percent polysaccharide. The continuous phase typically includes at least 5 weight percent, at least 10 weight percent, or at least 15 weight percent polysaccharide. In some embodiments, the continuous phase contains 5 to 50 weight percent, 5 to 40 weight percent, 10 to 40 weight percent, 5 to 30 weight percent, 10 to 30 weight percent, 5 to 25 weight percent, 10 to 25 weight percent, or 15 to 25 weight percent polysaccharide based on a total weight of the continuous phase.

The polysaccharide can be, for example, a water soluble starch or water soluble cellulose. Suitable water soluble starches and water soluble celluloses often have a viscosity in range of 6 to 10 centipoise for a 2 weight percent solution in water at room temperature (i.e., 20 to 25° C.). Water soluble starches are typically prepared by partial acid hydrolysis of starch. Examples of water soluble starches include those, for example, that are commercially available under the trade designation LYCOAT from Roquette (Lestrem, France). Examples of water soluble cellulose include, but are not limited to, alkyl cellulose (e.g., methyl cellulose, ethyl cellulose, ethyl methyl cellulose), hydroxylalkyl cellulose (e.g., hydroxymethyl cellulose, hydroxyethyl cellulose, hydroxypropyl cellulose, hydroxypropyl methyl cellulose, hdyroxyethyl methyl cellulose, hydroxyethyl ethyl cellulose), and carboxylalkyl cellulose (e.g., carboxymethyl cellulose).

The reaction mixture includes a dispersed phase in the continuous phase. The dispersed phase is typically in the form of droplets within the continuous phase and includes both a monomer mixture and polypropylene glycol. Within each droplet, the monomer mixture is polymerized to form polymeric particles. The polypropylene glycol acts as a porogen that gets partially entrapped within the polymeric particles. Because the polypropylene glycol has no polymerizable group, this material can be removed after formation of the polymeric particles. Pores (i.e., void volume or free volume) are created when the previously entrapped polypropylene glycol is removed.

The monomer mixture of the dispersed phase includes at least two monomers. As used herein, the term "monomer" refers to a reactant having a polymerizable group. The first monomer typically has a single polymerizable group. The second monomer has two polymerizable groups. The polymerizable groups are ethylenically unsaturated groups and are typically (meth)acryloyl groups, which are monovalent groups of formula $H_2C\!=\!CR^1\!-\!(CO)\!-\!$ where $R^1$ is hydrogen or methyl and (CO) denotes a carbonyl group with the oxygen and carbon connected by a double bond. In many embodiments, all of the monomers in the monomer mixture have (meth)acryloyl groups as the polymerizable groups. As used herein, the term "(meth)acrylate" includes both acrylate and methacrylate monomers. The ethylenically unsaturated groups are subjected to free radical polymerization to form polymeric particles.

The first monomer has negligible solubility in the continuous phase and has a single polymerizable group such as a (meth)acryloyl group. Some suitable first monomers include those of Formula (I).

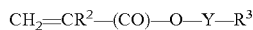  (I)

In this formula, group $R^2$ is hydrogen or methyl. In many embodiments, $R^2$ is hydrogen. Group Y is a single bond, alkylene, oxyalkylene, or poly(oxyalkylene). Group $R^3$ is a carbocyclic group or heterocyclic group.

As used herein, the term "alkylene" refers to a divalent group that is a radical of an alkane and includes groups that are linear, branched, cyclic, bicylic, or a combination thereof. As used herein, the term "oxyalkylene" refers to a divalent group that is an oxy group bonded directly to an alkylene group. As used herein, the term "poly(oxyalkylene)" refers to a divalent group having multiple oxyalkylene groups. Suitable Y alkylene and oxyalkylene groups typically have 1 to 20 carbon atoms, 1 to 16 carbon atoms, 1 to 12 carbon atoms, 1 to 10 carbon atoms, 1 to 8 carbon atoms, 1 to 6 carbon atoms, or 1 to 3 carbon atoms. Suitable poly(oxyalkylene) groups typically have 2 to 20 carbon atoms, 2 to 16 carbon atoms, 2 to 12 carbon atoms, 2 to 10 carbon atoms, 2 to 8 carbon atoms, 2 to 6 carbon atoms, or 2 to 4 carbon atoms.

Carbocyclic $R^3$ groups can have a single ring or can have multiple rings such as fused rings or bicyclic rings. Each ring can be saturated, partially unsaturated, or unsaturated. Each ring carbons can be unsubstituted or substituted with alkyl groups. Carbocyclic groups often has 5 to 12 carbon atoms, 5 to 10 carbon atoms, or 6 to 10 carbon atoms. Examples of carbocyclic groups include, but are not limited to, phenyl, cyclohexyl, cyclopentyl, isobornyl, and the like.

Heterocyclic $R^3$ groups can have a single ring or multiple rings such as fused rings or bicyic rings. Each ring can be saturated, partially unsaturated, or unsaturated. The heterocyclic group contains at least one heteroatom selected from oxygen, nitrogen, or sulfur. The heterocyclic group often has 3 to 10 carbon atoms and 1 to 3 heteroatoms, 3 to 6 carbon atoms and 1 to 2 heteroatoms, or 3 to 5 carbon atoms and 1 to 2 heteroatoms. Examples of heterocyclic rings include, but are not limited to, tetrahydrofurfuryl.

Exemplary monomers of Formula (I) for use as the first monomer include, but are not limited to, benzyl(meth)acrylate, 2-phenoxyethyl(meth)acrylate (commercially available from Sartomer under the trade designation SR339 and SR340), isobornyl(meth)acrylate, tetrahydrofurfuryl (meth)acrylate (commercially available from Sartomer under the trade designation SR285 and SR203), 3,3,5-trimethylcyclohexyl(meth)acrylate (commercially available from Sartomer under the trade designation CD421 and CD421A), and ethoxylated nonyl phenol acrylate (commercially available from Sartomer under then trade designation SR504, CD613, and CD612).

The second monomer in the monomer mixture has two polymerizable groups such as (meth)acryloyl groups. This monomer usually has negligible water solubility and/or is water dispersible. The second monomer is miscible with the first monomer in the monomer mixture and is typically of Formula (II).

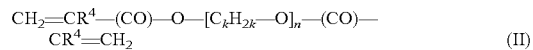  (II)

In Formula (II), group $R^4$ is hydrogen or methyl, the variable k is equal to either 2 or 3, and the variable n is an integer equal to at least 1. In some embodiments, the variable n is an integer no greater than 20, no greater than 16, no greater than 12, or no greater than 10. The number average molecular weight of the alkylene oxide portion of the monomer (i.e., the group $-\![C_kH_{2k}\!-\!O]_n\!-\!$) is often no greater 2000 grams/mole, no greater than 1200 grams/mole, no greater than 1000 grams, mole, no greater than 800 grams/mole, no greater than 600 grams/mole, no greater than 400 grams/mole, or no greater than 200 grams/mole.

Suitable monomers of Formula (II) are commercially available from Sartomer (Exton, Pa., USA) under the trade designation SR206 for ethylene glycol dimethacrylate, SR231 for diethylene glycol dimethacrylate, SR205 for triethylene glycol dimethacrylate, SR206 for tetraethylene glycol dimethacrylate, SR210 and SR210A for polyethylene glycol dimethacrylate, SR259 for polyethylene glycol (200) diacrylate, SR603 and SR344 for polyethylene glycol (400) di(meth)acrylate, SR252 and SR610 for polyethylene glycol (600) di(meth)acrylate, SR740 for polyethylene glycol (1000) dimethacrylate, and SR644 for propylene glycol (400) dimethacrylate.

In some embodiments, the only monomers in the monomer mixture are the first monomer and the second monomer. Any suitable amounts of the first monomer and second monomer can be used. The monomer mixture often contains 10 to 90 weight percent of the first monomer and 10 to 90 weight percent of the second monomer based on a total weight of the monomer mixture. For example, the dispersed phase can contain 20 to 80 weight percent of the first monomer and 20 to 80 weight percent of the second monomer, 25 to 75 weight percent of the first monomer and 25 to 75 weight percent of the second monomer, 30 to 70 weight percent of the first monomer and 30 to 70 weight percent of the second monomer, or 40 to 60 weight percent of the first monomer and 40 to 60 weight percent of the second monomer based on a total weight of the monomer mixture.

To provide polymeric particles with more rigidity, a third monomer having at least three polymerizable groups can be added to the monomer mixture. The polymerizable groups are typically an ethylenically unsaturated groups such as a (meth)acryloyl groups. In many embodiments, the third monomer has three (meth)acryloyl groups. This monomer usually has negligible water solubility and/or is water dispersible.

Suitable third monomers include, but are not limited to, ethoxylated trimethylolpropane tri(meth)acrylates such as ethoxylated (15) trimethylolpropane triacrylate (commercially available under the trade designation SR9035 from Sartomer) and ethoxylated (20) trimethylolpropane triacrylate (commercially available under the trade designation SR415 from Sartomer); propoxylated trimethylolpropane tri(meth)acrylates such as propoxylated (3) trimethylolpropane triacrylate (commercially available under the trade designation SR492 from Sartomer) and propoxylated (6) trimethylolpropane triacrylate (commercially available under the trade designation CD501 from Sartomer); tris(2-hydroxyethyl) isocyanurate tri(meth)acrylates such as tris (2-hydroxyethyl) isocyanurate triacrylate (commercially available under the trade designations SR368 and SR368D from Sartomer); and propoxylated glyceryl tri(meth)acrylates such as propoxylated (3) glycerol triacrylate (commercially available under the trade designation SR9020 and SR9020HP from Sartomer).

When a third monomer is present in the monomer mixture, any suitable amounts of the first monomer, second monomer, and third monomer can be used. The monomer mixture often contains 10 to 89 weight percent of the first monomer, 10 to 89 weight percent of the second monomer, and 1 to 20 weight percent of the third monomer based on a total weight of the monomer mixture. For example, the monomer mixture can contain 10 to 85 weight percent of the first monomer, 10 to 85 weight percent of the second monomer, and 5 to 20 weight percent of the third monomer. In other examples, the monomer mixture contains 20 to 75 weight percent of the first monomer, 20 to 75 weight percent of the second monomer, and 5 to 20 weight percent of the third monomer. In still other examples, the monomer mixture contains 30 to 65 weight percent of the first monomer, 30 to 65 weight percent of the second monomer, and 5 to 20 weight percent of the third monomer. In yet other examples, the monomer mixture contains 40 to 65 weight percent of the first monomer, 30 to 55 weight percent of the second monomer, and 5 to 20 weight percent of the third monomer.

In addition to the monomer mixture, the dispersed phase contains poly(propylene glycol). The poly(propylene glycol) is soluble in the monomer mixture within the dispersed phase but has negligible solubility in the continuous phase. The poly(propylene glycol) functions as a porogen that can be removed after polymerization to provide pores (e.g., void volumes or free volumes) in the polymeric particle. This poly(propylene glycol) does not have any polymerizable groups (i.e., it is not a monomer) and, in general, is not covalently attached to the polymeric particles that forms within the dispersed phase.

Any suitable molecular weight of poly(propylene glycol) can be used as the porogen. The molecular weight can affect the size of the pores that are formed in the polymeric particles. That is, the pore size tends to increase with the molecular weight of the poly(propylene glycol). The weight average molecular weight is often at least 500 grams/mole, at least 800 grams/mole, or at least 1000 grams/mole. The weight average molecular weight of the poly(propylene glycol) can be up to 10,000 gram/mole or greater. For ease of use, a poly(propylene glycol) that is a liquid at room temperature is often selected. Poly(propylene glycol) having a weight average molecular weight up to about 4000 g/mole or 5000 grams/mole tends to be a liquid at room temperature. Poly(propylene glycol) that is not a liquid at room temperature can be used if it is initially dissolved in a suitable organic solvent such as an alcohol (e.g., ethanol, n-propanol, or iso-propanol). The weight average molecular weight of the poly(propylene glycol) is often in a range of 500 to 10,000 grams/mole, in a range of 1000 to 10,000 grams/mole, in a range of 1000 to 8000 grams/mole, in a range of 1000 to 5000 grams/mole, in a range of 1000 to 4000 grams/mole.

The dispersed phase can contain up to 50 weight percent poly(propylene glycol). If higher amounts of the poly(propylene glycol) are used, there may be an insufficient amount of the monomer mixture included in the dispersed phase to form polymeric particles that are uniformly shaped. In many embodiments, the dispersed phase can contain up to 45 weight percent, up to 40 weight percent, up to 35 weight percent, up to 30 weight percent, or up to 25 weight percent poly(propylene glycol) based on a total weight of the dispersed phase. The dispersed phase typically contains at least 5 weight percent poly(propylene glycol). If lower amounts of the poly(propylene glycol) are used, the porosity of the resulting polymeric particles may be insufficient. That is, the void volume of the polymeric particles may be insufficient to adsorb and deliver an effective amount of an active agent. The dispersed phase typically can contain at least 10 weight percent, at least 15 weight percent, or at least 20 weight percent poly(propylene glycol). In some embodiments, the dispersed phase contains 5 to 50 weight percent, 10 to 50 weight percent, 10 to 40 weight percent, 10 to 30 weight percent, 20 to 50 weight percent, 20 to 40 weight percent, or 20 to 30 weight percent poly(propylene glycol) based on the total weight of the dispersed phase.

In some embodiments, the dispersed phase contains 50 to 90 weight percent monomer mixture and 10 to 50 weight percent poly(propylene glycol), 60 to 90 weight percent monomer mixture and 10 to 40 weight percent poly(propylene glycol), 50 to 80 weight percent monomer mixture and 20 to 50 weight percent poly(propylene glycol), or 60 to 80 weight percent monomer mixture and 20 to 40 weight percent poly(propylene glycol) based on a total weight of the dispersed phase.

In addition to the monomer mixture and poly(propylene glycol), the dispersed phase often contains an initiator for free radical polymerization of the monomer mixture. Any suitable initiator known in the art can be used. The initiator can be a thermal initiator, a photoinitiator, or both. The specific initiator used is often selected based on its solubility in the dispersed phase. The initiator is often used at a concentration of 0.1 to 5 weight percent, 0.1 to 3 weight percent, 0.1 to 2 weight percent, or 0.1 to 1 weight percent based on the weight of the monomer mixture.

When a thermal initiator is added to the reaction mixture, polymeric particles can be formed at room temperature (i.e., 20 to 25 degrees Celsius) or at an elevated temperature. The temperature needed for polymerization often depends on the particular thermal initiator used. Examples of thermal initiators include organic peroxides or azo compounds.

When a photoinitiator is added to the reaction mixture, polymeric particles can be formed by the application of actinic radiation. Suitable actinic radiation includes electromagnetic radiation in the infrared region, visible region, ultraviolet region, or a combination thereof.

Examples of photoinitiators suitable in the ultraviolet region include, but are not limited to, benzoin, benzoin alkyl ethers (e.g., benzoin methyl ether and substituted benzoin alkyl ethers such anisoin methyl ether), phenones (e.g., substituted acetophenones such as 2,2-dimethoxy-2-phenylacetophenone and substituted alpha-ketols such as 2-methyl-2-hydroxypropiophenone), phosphine oxides, polymeric photoinitiators, and the like.

Commercially available photoinitiators include, but are not limited to, 2-hydroxy-2-methyl-1-phenyl-propane-1-one (e.g., commercially available under the trade designation DAROCUR 1173 from Ciba Specialty Chemicals), a mixture of 2,4,6-trimethylbenzoyl-diphenyl-phosphine oxide and 2-hydroxy-2-methyl-1-phenyl-propan-1-one (e.g., commercially available under the trade designation DAROCUR 4265 from Ciba Specialty Chemicals), 2,2-dimethoxy-1,2-diphenylethan-1-one (e.g., commercially available under the trade designation IRGACURE 651 from Ciba Specialty Chemicals), a mixture of bis(2,6-dimethoxybenzoyl)-2,4,4-trimethyl-pentylphosphine oxide and 1-hydroxy-cyclohexyl-phenyl-ketone (e.g., commercially available under the trade designation IRGACURE 1800 from Ciba Specialty Chemicals), a mixture of bis(2,6-dimethoxybenzoyl)-2,4,4-trimethyl-pentylphosphine oxide (e.g., commercially available under the trade designation IRGACURE 1700 from Ciba Specialty Chemicals), 2-methyl-1[4-(methylthio)phenyl]-2-morpholinopropan-1-one (e.g., commercially available under the trade designation IRGACURE 907 from Ciba Specialty Chemicals), 1-hydroxy-cyclohexyl-phenyl-ketone (e.g., commercially available under the trade designation IRGACURE 184 from Ciba Specialty Chemicals), 2-benzyl-2-(dimethylamino)-1-[4-(4-morpholinyl)phenyl]-1-butanone (e.g., commercially available under the trade designation IRGACURE 369 from Ciba Specialty Chemicals), bis(2,4,6-trimethylbenzoyl)-phenylphosphine oxide (e.g., commercially available under the trade designation IRGACURE 819 from Ciba Specialty Chemicals), ethyl 2,4,6-trimethylbenzoyldiphenyl phosphinate (e.g., commercially available from BASF, Charlotte, N.C. under the trade designation LUCIRIN TPO-L), and 2,4,6-trimethylbenzoyldiphenylphosphine oxide (e.g., commercially available from BASF, Charlotte, N.C. under the trade designation LUCIRIN TPO).

The reaction mixture typically does not include a surfactant. The presence of a surfactant tends to increase the solubility of the monomers in the continuous phase. This can be detrimental to the formation of polymeric particles within the dispersed phase.

The reaction mixture often includes at least 10 percent dispersed phase and up to 90 weight percent continuous phase. In some embodiments, the reaction mixture contains 10 to 50 weight percent dispersed phase and 50 to 90 weight percent continuous phase, 10 to 40 weight percent dispersed phase and 60 to 90 weight percent continuous phase, 10 to 30 weight percent dispersed phase and 70 to 90 weight percent continuous phase.

To prepare the polymeric particles, droplets of the dispersed phase are formed in the continuous phase. The components of the dispersed phase are often mixed together prior to addition to the continuous phase. For example, the monomer mixture, initiator, and the poly(propylene glycol) can be blended together and then this blended composition can be added to the continuous phase. The resulting reaction mixture is often mixed under high shear to form a microemulsion. The size of the dispersed phase droplets can be controlled by the amount of shear or the mixing rate. The size of the droplets can be determined by placing a sample of the mixture under an optical microscope prior to polymerization. Although any desired droplet size can be used, the average droplet diameter is often less than 200 micrometers, less than 100 micrometers, less than 50 micrometers, less than 25 micrometers, less than 10 micrometers, or less than 5 micrometers. For example, the average droplet diameter can be in the range of 1 to 200 micrometers, 1 to 100 micrometers, 5 to 100 micrometers, 5 to 50 micrometers, 5 to 25 micrometers, or 5 to 10 micrometers.

If a photoinitiator is used the reaction mixture is often spread on a non-reactive surface to a thickness that can be penetrated by the desired actinic radiation. The reaction mixture is spread using methods that do not cause the droplets to coalesce. For example, the reaction mixture can be formed using an extrusion method. Often, the actinic radiation is in the ultraviolet region of the electromagnetic spectrum. If the ultraviolet radiation is applied from only the top surface of the reaction mixture layer, the thickness of the layer can be up to about 10 millimeters. If the reaction mixture layer is exposed to ultraviolet radiation from both the top and bottom surfaces, the thickness can be greater such as up to about 20 millimeters. The reaction mixture is subjected to the actinic radiation for a time sufficient to react the monomer mixture and form polymeric particles. The reaction mixture layer is often polymerized within 5 minutes, within 10 minutes, within 20 minutes, within 30 minutes, within 45 minutes, or within 1 hour depending on the intensity of the actinic radiation source and the thickness of the reaction mixture layer.

If a thermal initiator is used, the droplets can be polymerized while continuing to mix the reaction mixture. Alternatively, the reaction mixture can be spread on a non-reactive surface to any desired thickness. The reaction mixture layer can be heated from the top surface, from the bottom surface, or both to form the polymeric particles. The thickness is often selected to be comparable to that use with the use of actinic radiation such as ultraviolet radiation.

In many embodiments, a photoinitiator is preferred over a thermal initiator because lower temperatures can be used for polymerization. That is, the use of actinic radiation such as ultraviolet radiation can be used to minimize degradation of various components of the reaction mixture that might be sensitive to temperatures needed for use with thermal initiators. Further, the temperatures typically associated with the use of thermal initiators may undesirably alter the solubility of the various components of the reaction mixture between the continuous phase and the dispersed phase.

During the polymerization reaction, the monomer mixture reacts within the dispersed phase droplets suspended in the continuous phase. As the polymerization progresses, the poly(propylene glycol) included in the dispersed phase gets partially entrapped within the polymeric particle. Although it is possible that some portion of the poly(propylene glycol) can be covalently attached to the polymeric particle through a chain transfer reaction, preferably the porogen is not bonded to the polymeric particle.

After the polymeric particles have formed, they can be separated from the continuous phase. Any suitable separation method can be used. For example, water is often added to lower the viscosity of the continuous phase. The polymeric particles can be separated by decantation, filtration, or centrifugation. The polymeric particles can be further washed by suspending them in water and collecting them a second time by decantation, filtration, or centrifugation.

The polymeric particles can then be subjected to one or more washing steps to remove the poly(propylene glycol) porogen. Suitable solvents for removing the porogen include, for example, acetone, methyl ethyl ketone, toluene, and alcohols such as ethanol, n-propanol, or iso-propanol. Stated differently, the porogen is removed from the polymeric particles using solvent extraction methods. Pores are created where the porogen previously resided in the polymeric particles. The average diameter of the polymeric particles decreases upon removal of the porogen. In some embodiments, the average particle size decreases by at least 10 percent, at least 20 percent, at least 30 percent, or at least 50 percent with removal of the porogen.

In many embodiments, the resulting polymeric particles after removal of the porogen have an average diameter that is less than 200 micrometers, less than 100 micrometers, less than 50 micrometers, less than 25 micrometers, less than 10 micrometers, or less than 5 micrometers. For example, the polymeric particles can have an average diameter in the range of 1 to 200 micrometers, 1 to 100 micrometers, 5 to 100 micrometers, 5 to 50 micrometers, 5 to 25 micrometers, or 5 to 10 micrometers.

The resulting polymeric particles after removal of the porogen are typically suitable for adsorption of an active agent. Because of the hydrophobic nature of the monomers included in the monomer mixture used to form the polymeric particles, the polymeric particles are particularly suitable for adsorption of hydrophobic active agents. That is, the polymeric particles are typically hydrophobic and tend to readily adsorb hydrophobic active agents.

Some active agents of particular interest are biologically active agents. As used herein, the term "biologically active agent" refers to a compound that has some known effect on living systems such as, for example, a bacteria or other microorganism, plant, fish, insect, or mammal The bioactive agent is added for the purpose of affecting the living system such as affecting the metabolism of the living system. Examples of biologically active agents include, but are not limited to, medicaments, herbicides, insecticides, antimicrobial agents, disinfectants and antiseptic agents, local anesthetics, astringents, antifungal agents (i.e., fungicides), antibacterial agents, growth factors, herbal extracts, antioxidants, steroids or other anti-inflammatory agents, compounds that promote wound healing, vasodilators, exfoliants, enzymes, proteins, carbohydrates, and the like. Still other bioactive agents include artificial tanning agents, tanning accelerants, skin smoothing agents, skin tightening agents, anti-wrinkle agents, skin repair agents, anti-itch agents, hair growth agents, anti-acne agents, hair removal agents, corn removal agents, callus removal agents, wart removal agents, sunscreen agents, insect repellant agents, deodorants and antiperspirant agents, hair colorants or bleaching agents, and anti-dandruff agents. Any other suitable biologically active agent known in the art can be used. In some particular embodiments, the active agent are herbicides, insecticides, or fungicides.

Any suitable method can be used to adsorb the active agent into the polymeric particle once the porogen has been removed. In some embodiments, the active agent is a liquid and the polymeric particles are mixed with the liquid to adsorb the active agent. In other embodiments, the active agent can be dissolved in a suitable organic solvent and the polymeric particles are exposed to the resulting solution. The organic solvent is typically selected so that it does not dissolve the polymeric particles. When an organic solvent is used, at least some of the organic solvent may be adsorbed by the polymeric particle in addition to the active agent.

When the active agent is dissolved in an organic solvent, the concentration is typically selected to be as great as possible to shorten the time needed for adsorption of a suitable amount of the active agent onto the polymeric particle. The amount of active agent adsorbed and the amount of time required for adsorption are often dependent, for example, on the composition of the monomers used to form the polymeric particle, the rigidity of the polymeric particle (e.g., the amount of crosslinking), and the compatibility of the active agent for the polymeric particle. The adsorption time is often less than 24 hours, less than 18 hours, less than 12 hours, less than 8 hours, less than 4 hours, less than 2 hours, less than 1 hour, less than 30 minutes, less than 15 minutes, or less than 5 minutes. After adsorption, the particles are typically separated from the solution containing the active agent by decantation, filtration, or centrifugation.

The polymeric particles are particularly effective for storage of hydrophobic active agents. When contacted with hydrophobic active agents in a liquid form such as, for example, hydrophobic herbicides, hydrophobic insecticides, hydrophobic fungicides, or mixtures thereof, the hydrophobic active agents can be readily absorbed by the polymeric particles. Stated differently, the polymeric particles function like a sponge to adsorb the hydrophobic active agents.

The amount of active agent adsorbed can be up to 50 weight percent based on a total weight of the polymeric particle after adsorption (i.e., polymeric particles plus adsorbed active agent). In some example polymeric particles after adsorption, the amount of the active agent can be up to 40 weight percent, up to 30 weight percent, 25 weight percent, up to 20 weight percent, up to 15 weight percent, up to 10 weight percent, or up to 5 weight percent. Some polymeric particles after adsorption contain 1 to 50 weight percent active agent, 5 to 50 weight percent active agent, 1 to 40 weight percent active agent, 5 to 40 weight percent active agent, 10 to 40 weight percent active agent, or 20 to 40 weight percent active agent.

The polymeric particles with adsorbed active agent can be suspended in water. In some embodiments, the active agent is hydrophobic and is not extracted from the polymeric particles into the water. The suspension can be in the form of a lotion. The suspension (e.g., lotion) can contain up to 50 weight percent polymeric particles with adsorbed active agent. For example, the suspension can contain up to 40 weight percent, up to 30 weight percent, up to 25 weight percent, up to 20 weight percent, or up to 10 weight percent polymeric particles with adsorbed active agent.

The active agent is not covalently bonded to the polymeric particles. Under suitable diffusion controlled conditions, the active agent can be released from the polymeric particles. The release can be complete or nearly complete (e.g., greater than 90 percent, greater than 95 percent, greater than 98 percent, greater than 99 percent complete).

Various items are provided that include a reaction mixture, polymeric particles, a method of making polymeric particles, and a suspension containing the polymeric particles.

Item 1 is a reaction mixture that includes 1) a continuous phase and 2) a dispersed phase in the continuous phase. The continuous phase contains water and a polysaccharide dissolved in the water. The dispersed phase includes a) a monomer mixture and b) poly(propylene glycol). The monomer mixture contains i) a first monomer that is hydrophobic and that has an ethylenically unsaturated group and ii) a second monomer that is a poly(alkylene oxide) di(meth)acrylate and that is miscible with the first monomer. The poly(propylene glycol) has a weight average molecular weight of at least 500 grams/mole and is miscible with the first monomer and the second monomer.

Item 2 is the reaction mixture of item 1, wherein the continuous phase comprises 10 to 30 weight percent polysaccharide based on a total weight of the continuous phase.

Item 3 is the reaction mixture of item 1 or 2, wherein the reaction mixture comprises 10 to 50 weight percent dispersed phase based on a total weight of the reaction mixture.

Item 4 is the reaction mixture of any one of items 1 to 3, wherein the monomer mixture comprises 10 to 90 weight percent first monomer and 10 to 90 weight percent second monomer based on a total weight of the monomer mixture.

Item 5 is the reaction mixture of any one of items 1 to 4, wherein the monomer mixture further comprises a third monomer having at least 3 (meth)acryloyl groups.

Item 6 is the reaction mixture of item 5, wherein the dispersed phase comprises 10 to 89 weight percent first monomer, 10 to 89 weight percent second monomer, and 1 to 20 weight percent third monomer based on a total weight of the monomer mixture.

Item 7 is the reaction mixture of any one of items 1 to 6, wherein the dispersed phase comprises 50 to 90 weight percent monomer mixture and 10 to 50 weight percent poly(propylene glycol) based on a total weight of the dispersed phase.

Item 8 is the reaction mixture of any one of items 1 to 7, wherein the weight average molecular weight of the poly(propylene glycol) is in a range of 500 to 10,000 grams/mole.

Item 9 is a method of making a polymeric particle. The method includes preparing a blended composition that contains a) a monomer mixture and b) a poly(propylene glycol). The monomer mixture contains i) a first monomer that is hydrophobic and that has an ethylenically unsaturated group and ii) a second monomer that is a poly(alkylene oxide) di(meth)acrylate and that is miscible with the first monomer. The poly(propylene glycol) has a weight average molecular weight of at least 500 grams/mole and is miscible with the first monomer and the second monomer. The method further includes forming a reaction mixture by dispersing the blended composition in a continuous phase containing water and a polysaccharide dissolved in the water. The method still further includes curing the monomer mixture within the reaction mixture to form polymeric particles containing poly(propylene glycol) and then removing the poly(propylene glycol) from the polymeric particles to form pores within the polymeric particles.

Item 10 is the method of item 9, further comprising adsorbing a hydrophobic active agent within the free volume of the polymeric particles to form active agent-containing polymeric particles.

Item 11 is the method of item 10, further comprising suspending the active-containing polymeric particles in aqueous medium.

Item 12 is the method of item 10 or 11, wherein the active agent is biologically active.

Item 13 is the method of any one of items 9 to 12, wherein the reaction mixture comprises 10 to 50 weight percent dispersed phase based on a total weight of the reaction mixture.

Item 14 is the method of any one of items 9 to 13, wherein the monomer mixture comprises 10 to 90 weight percent first monomer and 10 to 90 weight percent second monomer based on a total weight of the monomer mixture.

Item 15 is the method of any one of items 9 to 14, wherein the monomer mixture further comprises a third monomer having at least 3 (meth)acryloyl groups.

Item 16 is the method of item 15, wherein the dispersed phase comprises 10 to 89 weight percent first monomer, 10 to 89 weight percent second monomer, and 1 to 20 weight percent third monomer based on a total weight of the monomer mixture.

Item 17 is the method of any one of items 9 to 16, wherein the dispersed phase comprises 50 to 90 weight percent monomer mixture and 10 to 50 weight percent poly(propylene glycol) based on a total weight of the dispersed phase.

Item 18 is the method of any one of items 9 to 17, wherein the weight average molecular weight of the poly(propylene glycol) is in a range of 500 to 10,000 grams/mole.

Item 19 is the method of any one of items 9 to 18, wherein the continuous phase comprises 10 to 30 weight percent polysaccharide based on a total weight of the continuous phase.

Item 20 is a polymeric particle that includes the reaction product of a monomer mixture that contains i) a first monomer that is hydrophobic and that has an ethylenically unsaturated group and ii) a second monomer that is a poly(alkylene oxide) di(meth)acrylate and that is miscible with the first monomer. The polymeric particles have pores containing poly(propylene glycol) or a hydrophobic active agent.

Item 21 is the polymeric particles of item 20, wherein the hydrophobic active agent is biologically active.

Item 22 is the polymeric particles of item 20 or 21, wherein the polymeric particles comprise 10 to 50 weight percent poly(propylene glycol) or hydrophobic active agent based on a total weight of the polymeric particles.

Item 23 is the polymeric particles of any one of items 20 to 22, wherein the average diameter of the polymeric particles is in a range of 1 to 200 micrometers.

Item 24 is the polymeric particle of any one of items 20 to 23, wherein the average diameter of the polymeric particles is in a range of 5 to 20 micrometers.

Item 25 is a suspension comprising water and up to 50 weight percent polymeric particles based on a total weight of the suspension. The polymeric particle includes the reaction product of a monomer mixture that contains i) a first monomer that is hydrophobic and that has an ethylenically unsaturated group and ii) a second monomer that is a poly(alkylene oxide) di(meth)acrylate and that is miscible with the first monomer. The polymeric particles have pores containing a hydrophobic active agent.

Item 26 is the suspension of item 25, wherein the hydrophobic active agent is a biologically active agent.

Item 27 is the suspension of item 25 or 26, wherein the hydrophobic active agent is a herbicide, insecticide, or fungicide.

EXAMPLES

Unless otherwise noted, all chemicals used in the examples can be obtained from Sigma-Aldrich Corp. (Saint Louis, Mo.).

TABLE 1

Glossary of Materials

| Material | Description |
| --- | --- |
| SR 339 | Trade designation for 2-phenoxyethyl acrylate ester obtained from Sartomer Company, Inc. (Exton, PA, USA) |
| SR 6030 | Trade designation for polyethylene glycol 400 dimethacrylate with a weight average molecular weight of 400 grams/mole obtained from Sartomer Company, Inc. (Exton, PA, USA) |
| SR 368 | Trade designation for tris(2-hydroxy ethyl) isocyanurate triacrylate ester obtained from Sartomer Company, Inc. (Exton, PA, USA) |
| SR 206 | Trade designation for ethylene glycol dimethacrylate ester obtained from Sartomer Company, Inc. (Exton, PA, USA) |
| PPG | Polypropylene glycol having a weight average molecular weight of 4000 grams/mole obtained from Alfa Aesar (Ward Hill, MA, USA) |
| IRGACURE 819 | Trade designation for the photoinitiator bis(2,4,6-trimethylbenzoyl)-phenylphosphineooxide obtained from BASF (Florham Park, NJ, USA) |
| HPMC | Hydroxypropyl methyl cellulose obtained from Sigma Aldrich (St. Louis, MO, USA) |
| IPA | Isopropyl alcohol obtained from Sigma Aldrich (St. Louis, MO, USA) |
| DEET | N,N-diethyl-meta-toluamide obtained from Alfa Aesar (Ward Hill, MA, USA) |

Example 1

The monomers SR 339 (5 grams) and SR 6030 (5 grams) were mixed with PPG (4.3 grams) and IRGACURE 819 (20 milligrams). The mixture was stirred vigorously for 20 minutes on gentle heat of about 40 to 50° C. This mixture was then added to 190 grams of 20 weight percent HPMC in water. The mixture was shear mixed for 20 minutes. The mixture was then spread thin on a surface of a polyethylene terephthalate film having a thickness of 100 micrometers. Such film is commercially available from DuPont (Wilmington, Del., US) under the trade designation ST 500. The mixture was cured with ultraviolet light for 15 to 20 minutes with a 100 Watts, long-wavelength BLACK RAY UV lamp (obtained from UVP, LLC of Upland, Calif., USA) situated at about 15 centimeters (6 inches) from the surface of the curing reaction mixture.

The cured mixture was then dispersed in excess water (400 mL), shaken for 30 minutes, and centrifuged at 3000 rpm in an EPPENDORF 5810 R centrifuge (obtained from Eppendorf in Germany). The supernatant containing HPMC was removed and the resulting polymeric particles were then re-suspended in 50 mL of water for a second rinse followed by centrifugation. After this, the polymeric particles were suspended in a 50 mL isopropyl alcohol and shaken for 20 minutes. This extracted the PPG and left voids (i.e., pores or free volume) in the polymeric particles. The polymeric particles were then centrifuged at 300 rpm for 30 minutes and the supernatant was discarded. The void volume (i.e., pore volume) in the polymeric particles was equivalent to the volume of PPG removed.

FIG. 1 is a scanning electron micrograph at 500× magnification of the polymeric particles prior to removal of PPG. FIG. 2 is a scanning electron micrograph at 500× magnification of the polymeric particles after removal of PPG. FIG. 3 is a scanning electron micrograph at 5000× magnification of the polymeric particles after removal of PPG.

Example 2

The monomers SR 339 (4 grams) and SR 368 (3 grams) and SR 206 (1 gram) were mixed with PPG (4.3 grams) and IRGACURE 819 (20 milligrams). The mixture was stirred vigorously for 20 minutes on gentle heat of about 40 to 50° C. This mixture was then added to 190 grams of 20 weight percent HPMC in water. The mixture was shear mixed for 20 minutes. The mixture was then spread thin on a surface of a polyethylene terephthalate film having a thickness of 100 micrometers. The mixture was cured with ultraviolet light for 15 to 20 minutes with a 100 Watts, long-wavelength BLACK RAY UV lamp (obtained from UVP, LLC of Upland, Calif., USA) situated at about 15 centimeters from the surface of the curing material.

The cured mixture was then dispersed in excess water (400 mL), shaken for 30 minutes, and centrifuged at 3000 rpm in an EPPENDORF 5810 R centrifuge. The supernatant containing HPMC was removed and the resulting polymeric particles were then re-suspended in 50 mL of water for a second rinse followed by centrifugation. After this, the polymeric particles were suspended in a 50 mL isopropyl alcohol and shaken for 20 minutes. This extracted the PPG and left voids (i.e., pores or free volume) in the polymeric particles. The polymeric particles were then centrifuged at 300 rpm for 30 minutes and the supernatant was discarded. The void volume (i.e., pore volume) in the polymeric particles was equivalent to the volume of PPG removed.

Example 3

Polymeric particles (1 gram), which were prepared as described in Example 1, were mixed with liquid DEET (0.2 grams). The liquid DEET was completely adsorbed by the polymeric particles. After adsorption, the polymeric particles contained 17 weight percent DEET.

The polymeric particles with adsorbed DEET were combined with water (3 grams) to form a lotion. This lotion was then extracted with acetone and analyzed by gas chromatography-mass spectroscopy (GC-MS). The extraction of DEET was 100 percent.

More specifically, 100 mg of the lotion was mixed with 10 mL acetone. The mixture was shaken for 20 hours on a mechanical wrist action shaker and then centrifuged (6000 revolutions per minute for 10 minutes). The sample was diluted further as needed to get within the response range of the calibration curve for DEET. GC-MS analysis was carried out using a system commercially available from Hewlett Packard (Model HP6890) that was operated in the electron impact mode. The sample was separated using a 30 meter AGILENT J&W DB-5MS 122-5532 capillary column. The column temperature was increased from 40° C. (1 minute hold time) to 310° C. at a linear rate of 10° C/minute with a final hold time of 5 minutes. Helium was used as the carrier gas with a constant flow rate of 1.5 mL/minute. The sample size was 10 microliters. The injector was operated with a split ratio of 40:1 and was heated to 250° C. The retention time for DEET was 15.1 minutes.

What is claimed is:

1. A reaction mixture for forming microporous particles comprising:
   a continuous phase comprising water and a polysaccharide dissolved in the water;
   a dispersed phase in the continuous phase, the dispersed phase comprising
   a) a monomer mixture comprising
      i) a first monomer having one ethylenically unsaturated group, wherein the first monomer is hydrophobic, the first monomer being of Formula (I)

$$CH_2=CR^2—(CO)—O—Y—R^3 \quad (I)$$

wherein
      $R^2$ is hydrogen or methyl;
      Y is a single bond, alkylene, oxyalkylene, or poly(oxyalkylene); and
      $R^3$ is a carbocyclic group or heterocyclic group; and
      ii) a second monomer that is miscible with the first monomer, the second monomer being of Formula (II)

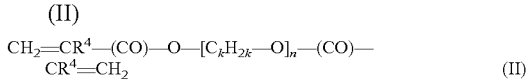

$$CH_2=CR^4—(CO)—O—[C_kH_{2k}—O]_n—(CO)—CR^4=CH_2 \quad (II)$$

wherein
      $R^4$ is hydrogen or methyl;
      k is equal to either 2 or 3; and
      n is an integer in a range of 1 to 20;
   b) a poly(propylene glycol) having a weight average molecular weight of at least 500 grams/mole, wherein the poly(propylene glycol) is miscible with the first monomer and the second monomer; and
   c) a photoinitator.

2. The reaction mixture of claim 1, wherein the continuous phase comprises 10 to 30 weight percent polysaccharide based on a total weight of the continuous phase.

3. The reaction mixture of claim 1, wherein the reaction mixture comprises 10 to 50 weight percent dispersed phase based on a total weight of the reaction mixture.

4. The reaction mixture of claim 1, wherein the monomer mixture comprises 10 to 90 weight percent first monomer and 10 to 90 weight percent second monomer based on a total weight of the monomer mixture.

5. The reaction mixture of claim 1, wherein the monomer mixture further comprises a third monomer having at least 3 (meth)acryloyl groups.

6. The reaction mixture of claim 5, wherein the dispersed phase comprises 10 to 89 weight percent first monomer, 10 to 89 weight percent second monomer, and 1 to 20 weight percent third monomer based on a total weight of the monomer mixture.

7. The reaction mixture of claim 1, wherein the dispersed phase comprises 50 to 90 weight percent monomer mixture and 10 to 40 weight percent poly(propylene glycol) based on a total weight of the dispersed phase.

8. The reaction mixture of claim 1, wherein the weight average molecular weight of the poly(propylene glycol) is in a range of 500 to 10,000 grams/mole.

9. A method of making a polymeric microporous particle, the method comprising:
   preparing a blended composition comprising
   a) a monomer mixture comprising
      i) a first monomer having one ethylenically unsaturated group, wherein the first monomer is hydrophobic, the first monomer being of Formula (I)

$$CH_2=CR^2—(CO)—O—Y—R^3 \quad (I)$$

wherein
      $R^2$ is hydrogen or methyl;
      Y is a single bond, alkylene, oxyalkylene, or poly(oxyalkylene); and
      $R^3$ is a carbocyclic group or heterocyclic group; and
      ii) a second monomer that is miscible with the first monomer, the second monomer being of Formula (II)

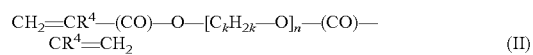

$$CH_2=CR^4—(CO)—O—[C_kH_{2k}—O]_n—(CO)—CR^4=CH_2 \quad (II)$$

wherein
      $R^4$ is hydrogen or methyl;
      k is equal to either 2 or 3; and
      n is an integer in a range of 1 to 20;
   b) a poly(propylene glycol) having a weight average molecular weight of at least 500 grams/mole, wherein the poly(propylene glycol) is miscible with the first monomer and the second monomer; and
   c) a photoinitator;
   forming a reaction mixture by dispersing the blended composition in a continuous phase comprising water and a polysaccharide dissolved in the water;
   curing the monomer mixture within the reaction mixture by exposure to actinic radiation to form polymeric particles containing poly(propylene glycol); and
   removing the poly(propylene glycol) from the polymeric particles to form pores within the polymeric particles.

10. The method of claim 9, further comprising adsorbing a hydrophobic active agent within the free volume of the polymeric particles to form active agent-containing polymeric particles.

11. The method of claim 10, further comprising suspending the active-containing polymeric particles in aqueous medium.

12. The method of claim 10, wherein the active agent is biologically active.

13. A polymeric microporous particle comprising the reaction product of the reaction mixture of claim 1 wherein the polymeric particles have pores containing poly(propylene glycol) or a hydrophobic active agent.

14. The polymeric particles of claim 13, wherein the hydrophobic active agent is biologically active.

* * * * *

UNITED STATES PATENT AND TRADEMARK OFFICE
CERTIFICATE OF CORRECTION

PATENT NO. : 9,827,318 B2  
APPLICATION NO. : 14/356733  
DATED : November 28, 2017  
INVENTOR(S) : Hassan Sahouani Page 1 of 1

It is certified that error appears in the above-identified patent and that said Letters Patent is hereby corrected as shown below:

Column 1
Line 30, delete "2011/0123456 (Pandidt et al.)." and insert -- "2011/0123456 (Pandit et al.)." --, therefor.

Column 3
Line 31, delete "hdyroxyethyl" and insert -- hydroxyethyl --, therefor.

Column 4
Line 7, delete "bicylic," and insert -- bicyclic, --, therefor.
Line 22, delete "bicylic" and insert -- bicyclic --, therefor.
Line 30 (approx.), delete "bicycic" and insert -- bicyclic --, therefor.

Column 9
Line 60, after "mammal" insert -- . --.

Column 10
Line 2, delete "vascodilators," and insert -- vasodilators, --, therefor.

Column 13
Line 29 (approx.) (Table 1), delete "phenylphosphineooxide" and insert -- phenylphosphineoxide --, therefor.

Column 15
Line 52, in Claim 1, delete "photoinitator." and insert -- photoinitiator. --, therefor.

Column 16
Line 8, in Claim 7, delete "10 to 40" and insert -- 10 to 50 --, therefor.
Line 41 (approx.), in Claim 9, delete "photoinitator;" and insert -- photoinitiator; --, therefor.

Signed and Sealed this  
Twenty-second Day of May, 2018

Andrei Iancu  
*Director of the United States Patent and Trademark Office*